US00PP36526P2

(12) United States Plant Patent
Schulze et al.

(10) Patent No.: US PP36,526 P2
(45) Date of Patent: Mar. 4, 2025

(54) ***HYDRANGEA* PLANT NAMED 'Bailpanthree'**

(50) Latin Name: *Hydrangea paniculata*
Varietal Denomination: Bailpanthree

(71) Applicant: Bailey Nurseries, Saint Paul, MN (US)

(72) Inventors: Justin Schulze, Athens, GA (US); Oren McBee, Bishop, GA (US); David Jonathan Roberts, Athens, GA (US)

(73) Assignee: BAILEY NURSERIES, Newport, MN (US)

( * ) Notice: Subject to any disclaimer, the term of this patent is extended or adjusted under 35 U.S.C. 154(b) by 0 days.

(21) Appl. No.: 18/800,032

(22) Filed: Aug. 10, 2024

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea paniculata* plant named 'Bailpanthree' that is characterized by its compact and densely branched plant habit, its very early blooming season, its range of panicle colors in both hot and cold climates; emerge green-white, turning to white then becomes blushed with pink, and then turns red in summer, and its thick foliage that is dark green in color and slightly twisted in form.

4 Drawing Sheets

Botanical classification: *Hydrangea paniculata.*
Varietal denomination: 'Bailpanthree'.

BACKGROUND OF THE INVENTION

The present invention relates to a new and distinct cultivar of *Hydrangea paniculata* and will be referred to hereafter by its cultivar name, 'Bailpanthree'. 'Bailpanthree' represents a new panicle *Hydrangea*, a perennial shrub grown for use as a landscape plant.

'Bailpanthree' was derived from an ongoing breeding program conducted by the Inventors in Cottage Grove, MN. The goals of the breeding program are to develop a new cultivar of *Hydrangea paniculata* with early flowering, and inflorescences that turn pink in hot summer climates.

'Bailpanthree' originated as a seedling that arose from seed planted from open pollination of an unnamed and unpatented plant of *Hydrangea paniculata* from the breeders' program designated as 'No. HP17-02-01' in summer of 2018. The male parent is therefore unknown. 'Bailpanthree' was selected as a single unique plant in summer of 2019 from the resulting seedlings.

Asexual propagation of the new cultivar was first accomplished by softwood stem cuttings by one of the Inventors in Winterville, Georgia in summer of 2020. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailpanthree' as a unique cultivar of *Hydrangea.*

1. 'Bailpanthree' exhibits a compact and densely branched plant habit.
2. 'Bailpanthree' exhibits a very early blooming season.
3. 'Bailpanthree' exhibits a range of panicle colors in both hot and cold climates; emerge green-white, turning to white then becomes blushed with pink, and then turns red in summer.
4. 'Bailpanthree' exhibits thick foliage that is dark green in color and slightly twisted in form.

The parent plant of 'Bailpanthree' differs from 'Bailpanthree' in having a larger plant size, panicles that are less dense and more lacey, lighter green leaves that are more prone to disease, and panicles that do not turn red in summer. 'Bailpanthree' can be most closely compared to the *Hydrangea paniculata* cultivars 'Bulk' (U.S. Plant Pat. No. 16,812) and 'Rensun' (U.S. Plant Pat. No. 25,438). 'Bulk' is similar to 'Bailpanthree' in having a early flowering and panicles that turn pink. 'Bulk' differs from 'Bailpanthree' in having panicles that are less dense and more lacey, panicles that turn a muted pink only and do not turn pink in hot climates, lighter green leaves that are not glossy, and a larger plant size. 'Rensun' is similar to 'Bailpanthree' in having a similar plant height and width and panicles that are full and white in color. 'Rensun' differs from 'Bailpanthree' in blooming later, foliage that is lighter green, less glossy, and in lacking twisting, and panicles that change to pink later and are less deep pink in color.

BRIEF DESCRIPTION OF THE DRAWINGS

The accompanying color photographs illustrate the overall appearance and distinct characteristics of the new *Hydrangea*. The photograph was taken of a one-year-old plant of 'Bailpanthree' as grown outdoors in a 1-quart container in Cottage Grove, Minnesota.

The photograph in FIG. 1 provides a side view of 'Bailpanthree' in bloom.

Figure 1:
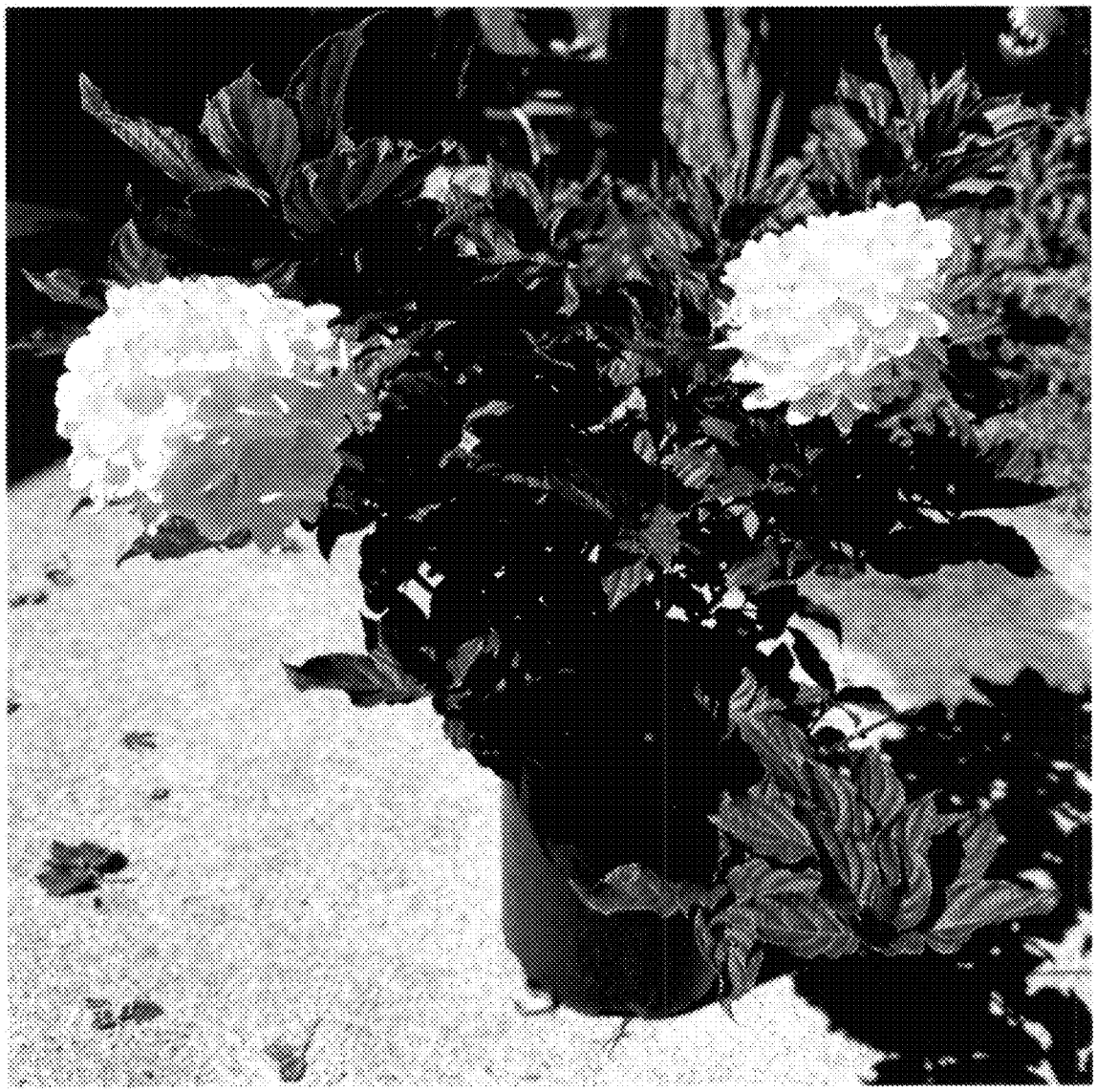
Figure 2:
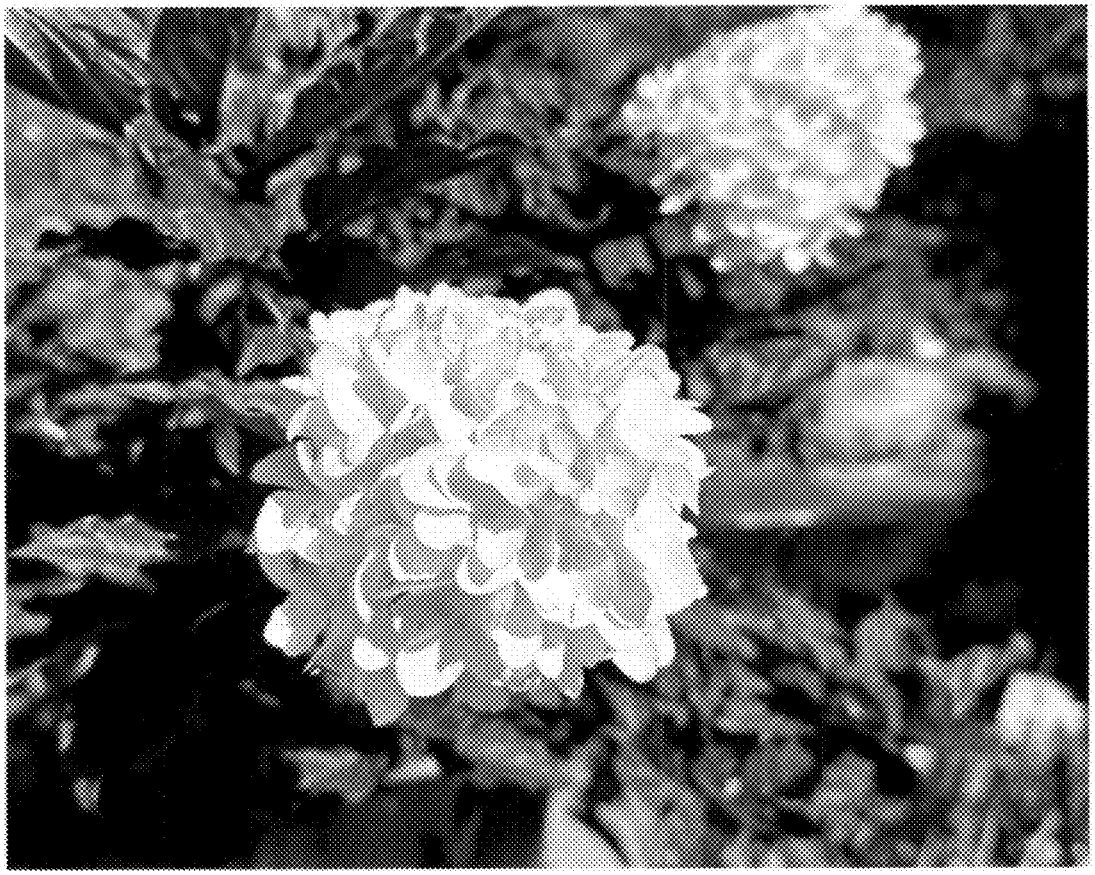

The photograph in FIG. 2 provides a provides a close-up view of a young inflorescence of 'Bailpanthree'.

Figure 3:
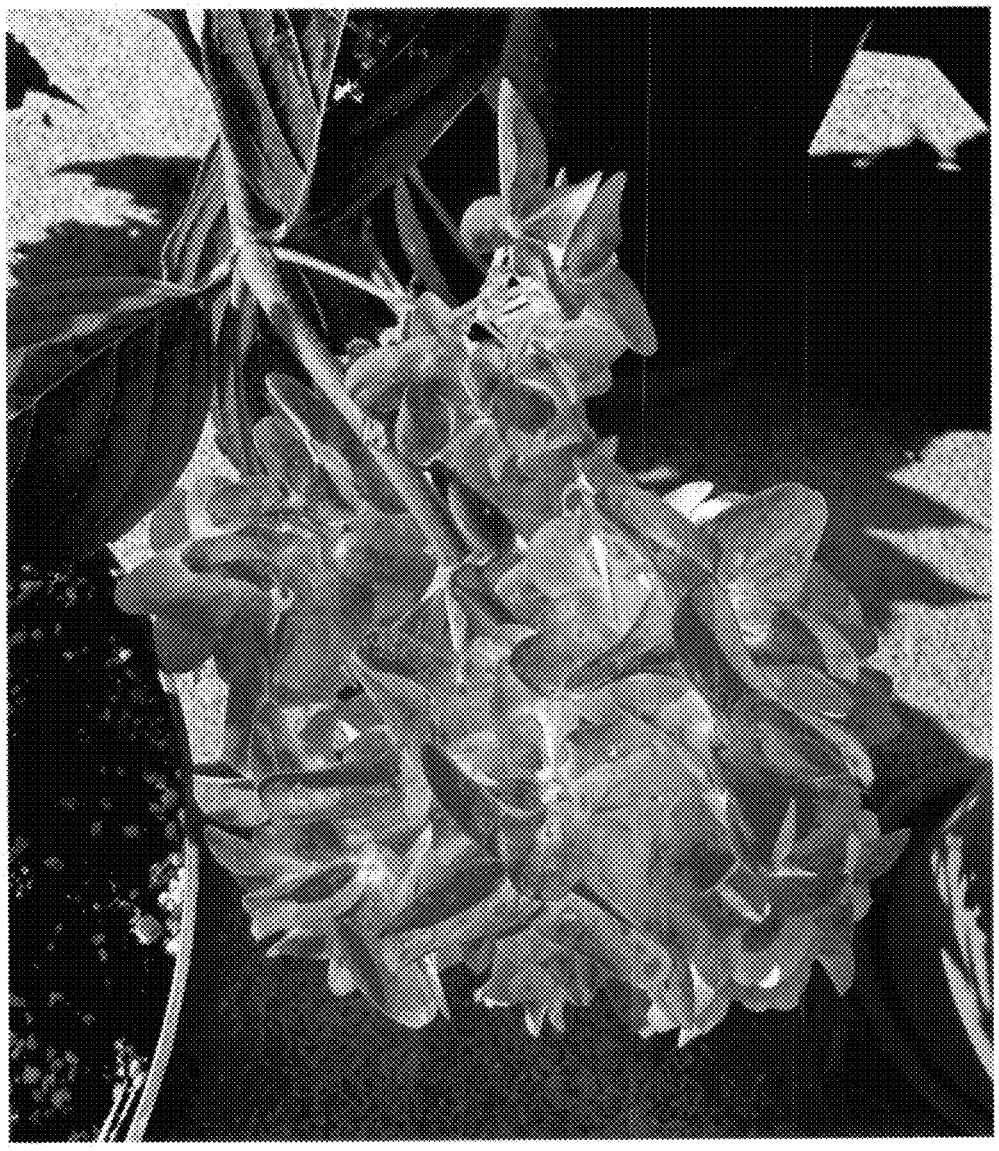

The photograph in FIG. 3 provides a provides a close-up view of a mature inflorescence of 'Bailpanthree'.

Figure 4:
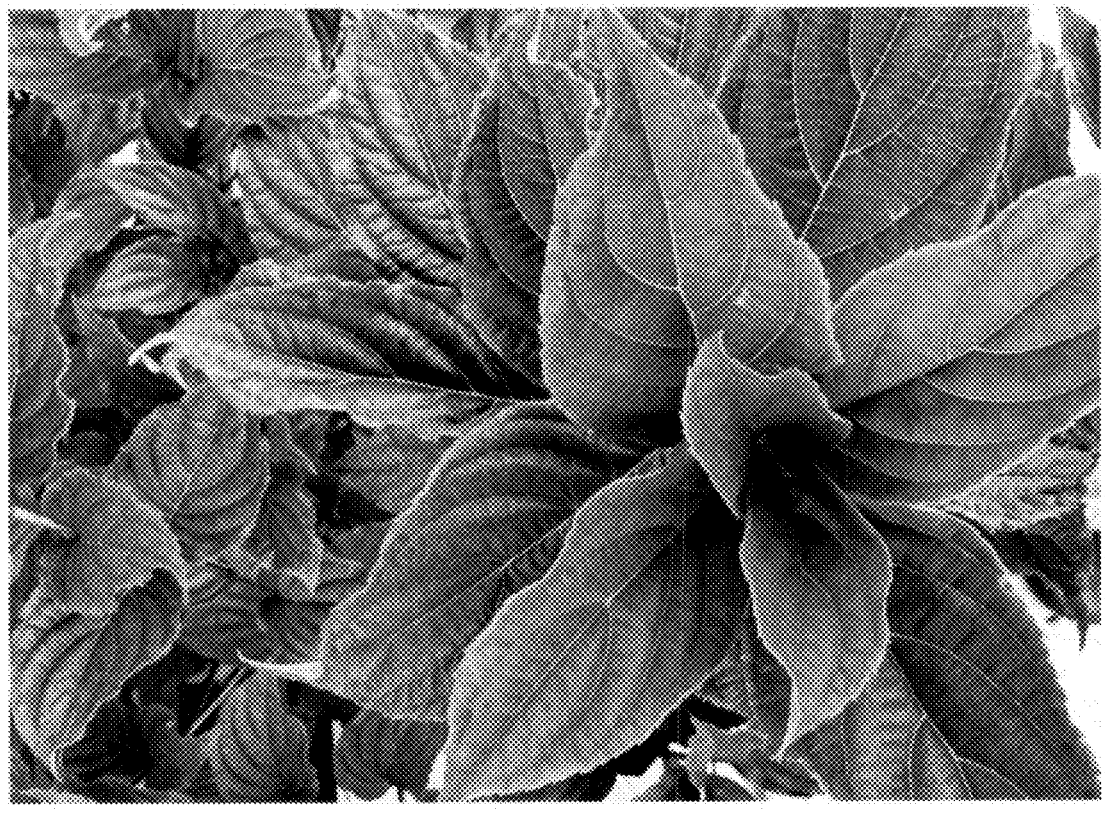

The photograph in FIG. 4. Provides a close-up view of the foliage of 'Bailpanthree'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of one-year-old plants of 'Bailpanthree' as grown outdoors in a 1-quart container in Cottage Grove, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late May to August in Winterville, Georgia.

*Plant type.*—Deciduous shrub, panicle type *Hydrangea.*

*Plant habit.*—Compact, densely branched.

*Height and spread.*—Average of 41 cm in height and 1 m in width as a 1-year-old plant grown in a container, reaches about 1.5 m in height and spread as a mature plant in the landscape.

*Cold hardiness.*—At least in U.S.D.A. Zone 4.

*Diseases and pests.*—No susceptibility and resistance to diseases or pests has been observed.

*Root description.*—Fine, fibrous and dense, 164B in color.

*Propagation.*—Softwood stem cuttings.

*Root development.*—An average of 20 days for root initiation with a young rooted plant produced in an average of 6 weeks.

*Growth rate and vigor.*—Moderate.

Branch description:

*Branch shape.*—Rounded to slightly quadrangular.

*Branch strength.*—Strong.

*Branch color.*—Young; 199A and heavily flushed towards the end with 182A, mature; 177A to 177B, old branches; striations of 161C and 200A, trunk; exfoliating 200A, 199B, and 158C.

*Branch size.*—Main; 7 cm in length, 1.2 cm in diameter, lateral; 36 cm in length, 5 mm in diameter, secondary; 16 cm in length, 3 mm in diameter.

*Branch surface.*—Young; slightly glossy with a waxy surface, mature; slightly exfoliating, glossy, sparsely covered with round shaped lenticels, an average of 1 mm in diameter, matches surface in color, trunk; exfoliating, glossy.

*Branch aspect.*—Upright to outward.

*Internode length.*—An average of 3 cm.

*Branching.*—Moderately branched, main; 1, lateral; 8, secondary; 4.

Foliage description:

*Leaf shape.*—Ovate, slightly twisting.

*Leaf arrangement.*—Opposite.

*Leaf division.*—Simple.

*Leaf base.*—Cuneate.

*Leaf apex.*—Apiculate, slightly twisting.

*Leaf margins.*—Serrate, moderately undulate.

*Leaf venation.*—Pinnate, color; upper surface 144A, lower surface 145C, main vein flushed with 185A.

*Leaf size.*—An average of 10 cm in length and 4.5 cm in width.

*Leaf attachment.*—Petiolate.

*Leaf number.*—An average of 20 (10 pairs) per lateral stem.

*Leaf surface.*—Young and mature upper and lower surface; glossy, rugose, mature upper surface; moderately covered with tiny, stiff pilose pubescence, 155D in color, 0.3 mm in length, mature lower surface; has a lustrous sheen, glabrous.

*Leaf color.*—Young upper surface; 144A, young lower surface; 146A, mature upper surface; 139A and 143A.

*Petioles.*—An average of 8 mm in length and 3 mm in width, flattened, top side concave, both surfaces glossy, densely covered with short, soft tangled floccose pubescence, color; upper and lower surfaces 183A, flushed with 202A.

Inflorescence description:

*Inflorescence type.*—Terminal conical panicle, comprised of single sterile flowers and fertile flowers.

*Lastingness of inflorescence.*—Sterile flowers; persistent for an average of 6 weeks, fertile flowers; self-cleaning, an average of 5 days.

*Inflorescence mumber.*—One per lateral stem.

*Inflorescence size.*—Up to 12 cm in height and diameter.

*Flower number.*—An average of 125 sterile flowers and 20 fertile flowers per panicle.

*Flower fragrance.*—None.

*Flower aspect.*—Sterile flowers; upright and outward, fertile flowers; held upright peduncle.

*Flower size.*—Sterile flowers; (including showy sepals) up to 4 cm in diameter and 8 mm in depth, fertile flowers; an average of 7 mm in diameter and 5 mm in depth.

*Flower type.*—Rotate.

*Peduncles.*—Primary peduncles; strong, flattened oval in shape, an average of 2 cm in length and 2 mm in width, 145B in color, secondary peduncles 8 mm in length and 2 mm in width, 157B in color, all peduncle surfaces are matte and densely covered with short, soft tangled floccose pubescence that match surface color.

*Pedicels.*—Sterile flowers; moderate strength, an average of 1.3 cm in length and 1 mm in width, NN155A in color, surfaces are matte and densely covered with short, soft tangled floccose pubescence that match surface color.

*Bracts.*—Located at the base of peduncles and pedicels, linear in shape, acute apex, 4 mm in length, 0.5 mm in width, color; NN155A, flushed with 61A and 63B.

*Petals.*—Sterile flowers; petal spot (flower bud); 2 mm in depth and 1 mm in diameter, round in shape, color; NN155A, becomes flushed with 73A, when petals open; average of 4, concave in shape, acute apex, cuneate base, entire margins, average of 2 mm in length, 1.5 mm in width, both surfaces are glabrous and matte, color: both surfaces when opening and fully open NN155B, fall colors; petals drop after full maturity, fertile flowers; petal spot (flower bud); 2 mm in depth, 1.5 mm in diameter, round in shape, color; NN155A, becomes flushed with 73A, when petals open; average of 5, rotate, concave in shape, acute apex, cuneate base, entire margins, 3 mm in length and 2 mm in width, both surfaces are glabrous, satiny, and matte, color: both surfaces when opening and fully open NN155D, petals drop after maturity.

*Sepals.*—Sterile flowers; 4, rotate, elliptical to ovate in shape, apex is rounded, base is cuneate, entire margins and slightly undulate, 2 cm in length, 1.5 cm in width, both surfaces glabrous, satiny, matte, slightly transparent, color: when opening upper and lower surface; 145A, when fully open upper and lower surface early spring; 157D and NN155A, late spring; 157A, becomes flushed with 73B and 62A, then turning fully to blend of 62A and 67A in late summer, fading at end of season; 165A, 165B and 158A, fertile flowers; average of 5, fused, 2% of top portion free, acute apex, broadly cuneate base, entire margins, 0.9 mm in length, 0.8 mm in width, surfaces are matte and glabrous, 157D and NN155A in color, becoming flushed with 187C.

Reproductive organs:

*Gynoecium.*—Sterile flowers; 1 pistil, an average of 1.8 mm in length, cone shaped, stigma; very small and fine, 0.3 mm in length, 155A in color, style; 1 mm in length, 158C in color, ovary is superior, 0.5 mm in depth, 158C in color, fertile flowers; 3 pistils, very minute, an average of 0.3 mm in length, stigma, style; minute, not distinguishable, ovary is superior, 2 mm in depth and diameter, 158C in color.

*Androecium.*—Sterile flowers; 8 stamens, filaments; an average of 2 mm in length and 155A in color, anthers; club-shaped, an average of 0.7 mm in diameter, 0.5 in depth, 155A in color, pollen; low, 158C in color, fertile flowers; 10 stamens, filaments; up to 4 mm in length and NN155C in color, anthers; bifid, broad oblong in shape, an average of 1 mm in width, 0.8 in depth, 158B in color, fading to 165A in color, pollen; moderate, 21A in color.

*Fruit and seed.*—None observed.

It is claimed:

1. A new and distinct cultivar of *Hydrangea* plant named 'Bailpanthree' substantially as herein illustrated and described.

* * * * *